(12) United States Patent
Marshall et al.

(10) Patent No.: US 6,579,095 B2
(45) Date of Patent: Jun. 17, 2003

(54) MATING PARTS SCANNING AND REGISTRATION METHODS

(75) Inventors: Michael C. Marshall, Savage, MN (US); Timothy W. Vadnais, Victoria, MN (US); Bruce W. Hultgren, Victoria, MN (US)

(73) Assignee: Geodigm Corporation, Chanhassen, MN (US)

( * ) Notice: Subject to any disclaimer, the term of this patent is extended or adjusted under 35 U.S.C. 154(b) by 0 days.

(21) Appl. No.: 09/746,468

(22) Filed: Dec. 22, 2000

(65) Prior Publication Data

US 2002/0081554 A1 Jun. 27, 2002

(51) Int. Cl.⁷ ................................................ A61C 11/00
(52) U.S. Cl. ........................................ 433/213; 433/49
(58) Field of Search .............................. 433/54, 73, 74, 433/213, 214, 49, 53, 55

(56) References Cited

U.S. PATENT DOCUMENTS

| 4,182,312 A | 1/1980 | Mushabac |
| 4,602,905 A | 7/1986 | O'Keefe, III |
| 4,611,288 A | 9/1986 | Duret et al. |
| 4,752,964 A | 6/1988 | Okada et al. |
| 4,837,732 A | 6/1989 | Brandestini et al. |
| 4,935,635 A | 6/1990 | O'Harra |
| 5,198,877 A | 3/1993 | Schulz |
| 5,224,049 A | 6/1993 | Mushabac |
| 5,338,198 A | 8/1994 | Wu et al. |
| 5,347,454 A | 9/1994 | Mushabac |
| 5,448,472 A | 9/1995 | Mushabac |
| 6,152,731 A * | 11/2000 | Jordan et al. .................. 433/69 |
| 6,200,135 B1 | 3/2001 | Hultgren |
| 6,206,693 B1 | 3/2001 | Hultgren |
| 6,217,334 B1 | 4/2001 | Hultgren |
| 6,227,851 B1 * | 5/2001 | Chishti et al. ................. 433/24 |
| 6,261,098 B1 * | 7/2001 | Persson ...................... 433/213 |
| 6,394,801 B2 * | 5/2002 | Chishti et al. ................. 433/24 |

OTHER PUBLICATIONS

Okumura et al., "CAD/CAM Fabrication of Occlusal Splints for Orthognathic Surgery", *JCO, Inc.*, vol. 33, No. 4, pp. 231–235 (Apr. 1999).

Web site "American Board of Orthodontics", http://www.americanboardortho.com/pages/28.htm, 14 pages (Nov. 8, 2000).

* cited by examiner

*Primary Examiner*—Ralph A. Lewis
(74) *Attorney, Agent, or Firm*—Merchant & Gould P.C.

(57) ABSTRACT

Methods for scanning and registering parts having complex geometries, such as dental study casts and mating housing shells for electronic devices, pacemakers, and other devices.

18 Claims, 14 Drawing Sheets

FIG. 13
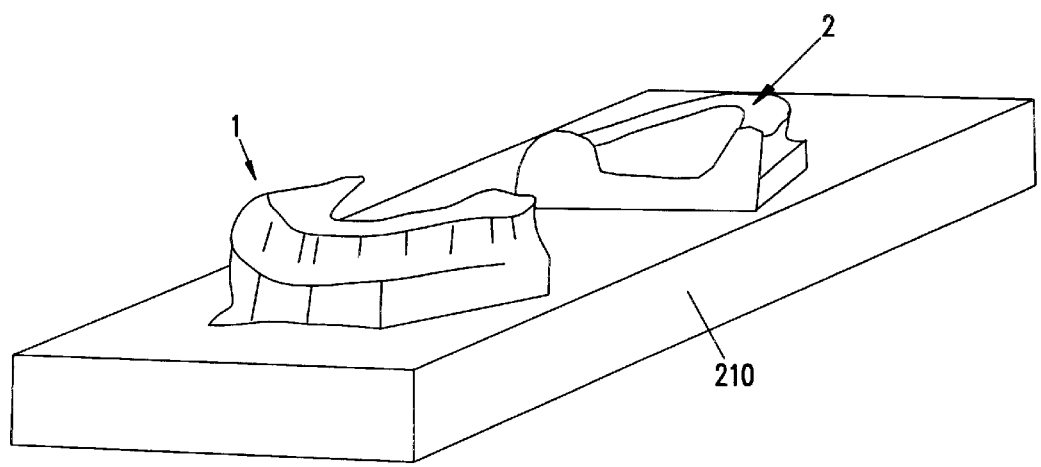
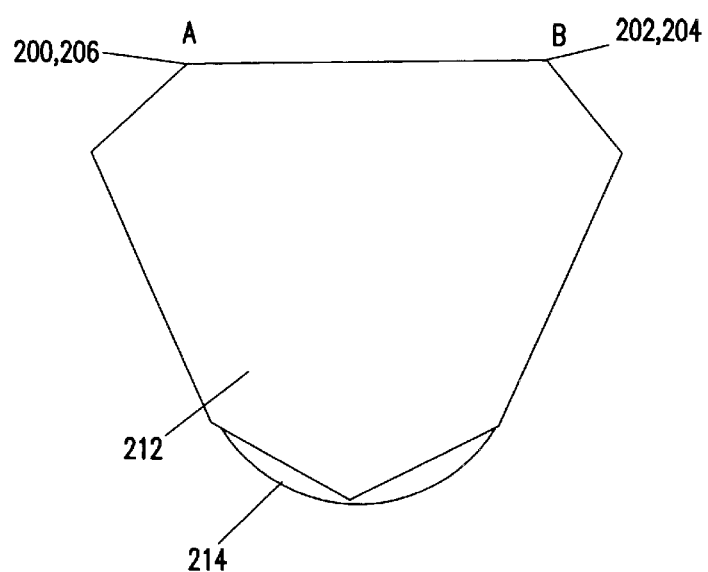
FIG. 14

MATING PARTS SCANNING AND REGISTRATION METHODS

FIELD OF THE INVENTION

The present invention relates generally to scanning of complex geometries. More particularly, the invention relates to methods to achieve bite registration of scanned images of dental study casts. The methods also have application in verifying the accuracy of mating parts, such as housings for electronic devices including cellular telephones and electronic organizers, and other housings of complex geometry such as a pacemaker housing.

BACKGROUND OF THE INVENTION

Dental study casts are an integral part of a dentist's understanding of how a patient's teeth and bite function in a static relationship. This static relationship serves three important functions. The primary function is one of a diagnostic function for interpretation of any discrepancies or problems that exist within the bite relationship. The second function is educational. For example, the study casts provide better communication as a concrete model while helping the patient understand any discrepancies that may exist in the way their teeth function in that static relationship. Third, the dental study casts serve an important medical/legal function in defining the pre-existing static bite relationship prior to the performance of any work. This work can be defined either from an oral surgical standpoint, prosthetic standpoint or orthodontic/periodontal standpoint.

Significant complications are associated with study casts, however, since the casts need to be stored for an extended period (generally seven years). For example, the storage of the study casts requires large amounts of space in humidity controlled environments, as well as extensive laboratory procedures involving OSHA guidelines and space utilization for the study casts to be constructed. In addition, a significant amount of turn-around time is required for the curing process of the plastic study casts to occur. In light of these significant constraints as well as the importance associated with having an accurate recording of the pre-existing bite relationship, there arises a need for an apparatus (or system) and method in which electronic image data can be collected from an impression to circumvent the need for storage of physical study casts.

As noted above, in order to study dental work to be performed on a patient's teeth, a working model of the teeth constructed of a plaster study cast is created. The plaster cast is based on a series of impressions taken to obtain the geometry of the teeth. To take an impression, alginate impression material is poured into a tray (i.e., an impression tray) which is then introduced into the patient's mouth for a period of time (typically one to two minutes). The impression material sets about the teeth and soft tissues forming a negative impression. The patient also bites into a soft material for registering a simultaneous imprint of the upper and lower set of teeth which records the relationship of the teeth in the upper and lower jaws respectively in three planes of space.

Once the impressions have set, they are sent to a lab to be processed into an upper and lower plaster study cast. The study casts are articulated together via the bite registration material to reproduce the bite of the patient. After construction, the study casts are returned to the dentist/orthodontist as a working study cast.

Formation of the study casts are governed by guidelines set by the American Board of Orthodontics (ABO). As illustrated in FIGS. 1A, 1B, the upper and lower study casts 1, 2 each comprise a base 3, 3' and a positive impression of the patient's teeth 4, 4'. Each base 3, 3' includes a rear surface 5, 5' and a bottom surface 6, 6'. The bases 3, 3' of the upper and lower casts 1, 2 are machined to a precise geometry illustrated in FIGS. 2A, 2B. The total height h of the two casts 1, 2, measured from the bottom surface 6 of the cast 1 to the bottom surface 6' of the other cast 2, is about 70 mm, and machining begins a distance d of about 13 mm from the bottom surfaces 6, 6' of each cast. Further, as illustrated in FIGS. 2A and 2B, the study casts include angled surfaces 7, 7' and 8, 8' that connect the rear surfaces 5, 5' to the side surfaces of the casts 1, 2. The angled surfaces have a length l of about 13 mm. A schematic illustration of the geometry of the casts is provided at the right hand side of FIGS. 2A and 2B, in which the angle $\alpha$ between each side surface and the rear surface 5 is about 70 degrees for the upper cast 1, while the angle $\beta$ between each side surface and the rear surface 5' is about 65 degrees for the lower cast 2.

A serious drawback of this method is the number of labor intensive steps required to produce the study casts, the space and legal storage requirements of the study casts, and the inability to interface the study casts interactively with other diagnosis information (e.g., photographs and radiographs). Accordingly, if additional work is required, the cast fails in some way or is damaged, and/or the cast is lost, then an additional impression series must be taken. The development of a set of electronic data from the series of dental impressions wherein only a single impression need be taken for multiple interactive functions would be beneficial.

In the past, several devices have been designed for the electronic imaging of teeth. Also, other devices are known which utilize numerical data to create prototype devices. While known examples of such systems and devices follow, generally such systems do not provide the accuracy required for orthodontic work. Instead, such systems are generally useful only for crowns, fillings, etc.

U.S. Pat. No. 4,182,312 generally discloses a dental probe having a stylus which is connected through a rod to a three position transducer. Three signals are produced for indicating the position of the probe at any point to which the probe is applied. The transducers are mounted on an index tray which is adapted to be fastened to the jaw of the patient. Thus the patient's jaw becomes the origin against which all measurements are made. Contact between the tip of the stylus and the patient's tissue completes a circuit to turn on a recording mechanism which receives the transducer's outputs.

U.S. Pat. No. 4,611,288 generally discloses a method of automatically producing dental prostheses (e.g., crowns, inlays, dentures and the like) using an optical impression taken of the oral region with nontraumatic radiation. The reflected waves are transformed into numerical data which is used to operate a numerically controlled machine in the fabrication process.

U.S. Pat. No. 4,752,964 generally discloses an apparatus for producing, from an object having a three-dimensional shape, a shape equivalent or analogous to the three-dimensional shape. Here, light is irradiated to the object in an optical cutting plane. The light is picked up by an image pick-up device, and two-dimensional positions of the light are obtained in a direction perpendicular to the optical cutting plane to determine its three dimensional shape.

U.S. Pat. No. 4,935,635 generally discloses a three-dimensional point measuring system which includes a laser diode for projecting a triangulating beam at a surface to be mapped, with the beam scanned repeatedly across the surface. Photodetectors detect the position of the beam as reflected from the mapped surface, given by triangulation Z-axis or depth information. Correlation of a particular point with the position of the scanner along the scan line gives Y-axis information, or information in a width direction. The scanner and diode are mounted on a slide or platform device which moves perpendicularly to the Y axis in the direction in and out of the mouth, driven by a stepper motor, and the monitored position of the stepper motor is coordinated with the other information on each spot to yield X-axis information.

U.S. Pat. No. 5,198,877 generally discloses a method and apparatus for optically sampling numerous points on the surface of an object to remotely sense its shape utilizing two stages. The first stage employs a moveable non-contact scanner, which in normal operation sweeps a narrow beam of light across the object, illuminating a single point of the object at any given instant in time. The location of that point relative to the scanner is sensed by multiple linear photodetector arrays behind lenses in the scanner. These sense the location by measuring the relative angular parallax of the point. The second stage employs multiple fixed but widely separated photoelectronic sensors to detect the locations of several light sources affixed to the scanner. Individual light sources are distinguished by time-multiplexing their on-off states. A coordinate computer calculates the absolute spatial positions where the scanner light beam is incident on the object to generate a computer model of the object.

U.S. Pat. No. 5,224,049 discloses a method for use in preparing a dental prosthesis and U.S. Pat. No. 5,347,454 generally discloses a system for use in preparing a dental prosthesis.

U.S. Pat. No. 5,448,472 discloses a method for collecting three-dimensional surface information in dental applications via a video camera. A tape strip is applied to a tooth surface to provide a distance reference or standard for use by a computer in analyzing the video data to determine actual distances. The tape strips are additionally provided with identification markings identifying the type of surfaces and the teeth to which the tape strips are attached.

Each of the foregoing systems, devices and methods suffer the drawback in that bulky, expensive specialized devices are required. The processes are extremely time consuming or require the introduction of devices into the patient's mouth for extended periods of time or which leads to patient discomfort. Also, these systems are limited to dental restorative procedures only. Reduced accuracy and precision of the measurements also greatly limit the usefulness of these systems to direct scanning of the dental impressions, study casts or both.

In addition, once a set of electronic data from a series of dental impressions has been taken, there exists a need to be able to accurately register the subsequently created maxilla and mandible scanned images to produce an accurate display of the patient's bite registration.

There exists a need for methods for achieving registration of maxilla and mandible study cast images in order to produce an accurate display of the bite registration of the patient.

SUMMARY OF THE INVENTION

The present invention provides methods for scanning and registering parts having complex geometries, such as dental study casts and mating housing shells for electronic devices, pacemakers, and other devices.

In one aspect of the invention, a bite registration method for maxilla and mandible study casts is provided. The method comprises scanning the maxilla and mandible study casts to create maxilla and mandible study cast images, and registering the maxilla and mandible study cast images.

In another aspect of the invention, a method of verifying a mating relationship between objects to be mated together is provided. The method comprises scanning the objects to create images of the objects, registering the object images by aligning a plurality of selected reference points associated with the object images, and bringing the registered object images together to a position representative of the mating relationship of the objects.

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying description, in which there is described a preferred embodiment of the invention.

BRIEF DESCRIPTION OF THE DRAWINGS

Referring to the drawings, wherein like numerals represent like parts throughout the several views:

FIG. 13 illustrates the maxilla and mandible study casts mounted on a cassette in implementing a third method in accordance with the present invention.

FIG. 14 is a top schematic view of the scanned images of the study casts in alignment according to the third method.

DETAILED DESCRIPTION OF THE PREFERRED EMBODIMENT

A detailed discussion of the present invention will be deferred pending a discussion of a scanning method used to create images of scanned dental study casts. Although the preferred embodiment is described in relation to achieving bite registration of scanned dental study cast images, it is to be realized that the methods described herein have applications in numerous other areas as well, including scanning and registering mating parts, such as molded housing for cellular phones, electronic organizers, pacemakers, and a host of other parts having complex geometries, in order to verify the accuracy of the molds and the molding process used to create the parts.

1. Overview

Figure 1B:
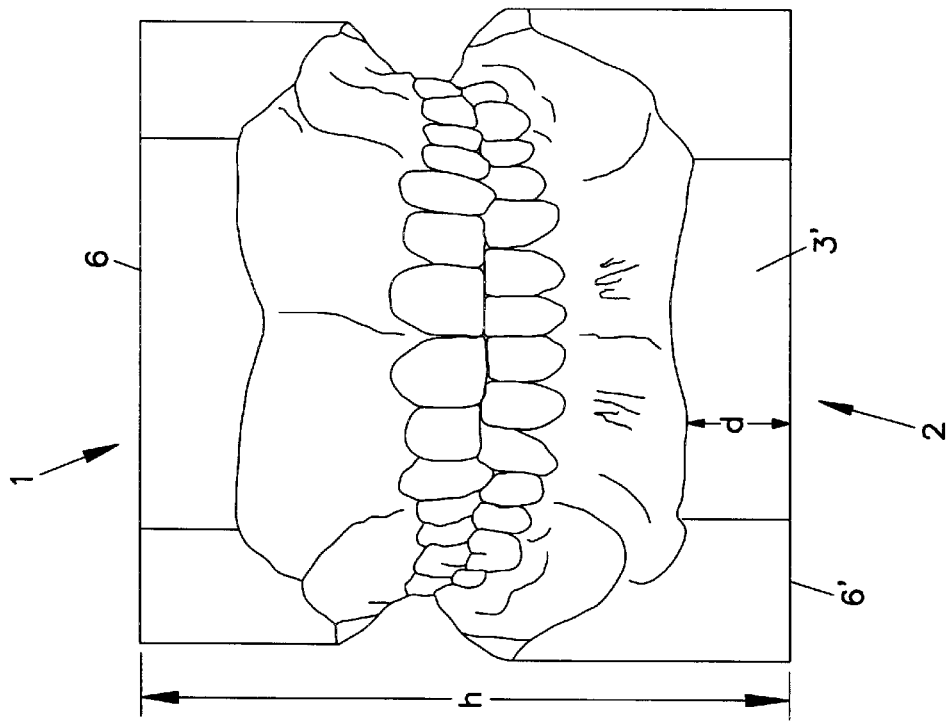
FIGS. 1A and 1B are side and front views, respectively, of maxilla and mandible dental study casts.
Figure 1A:
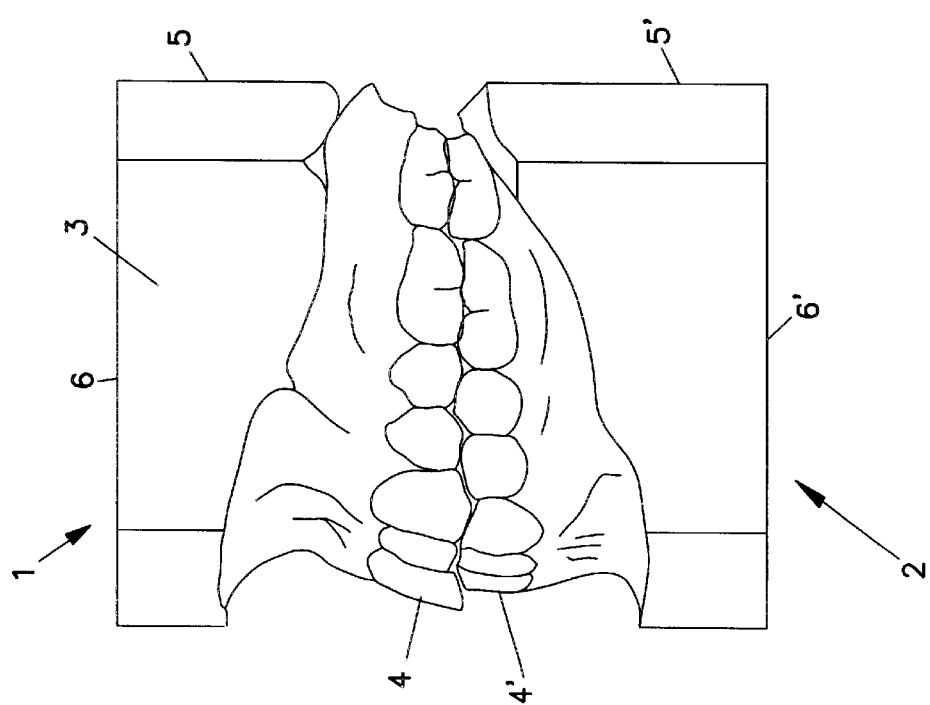
Figure 2A:
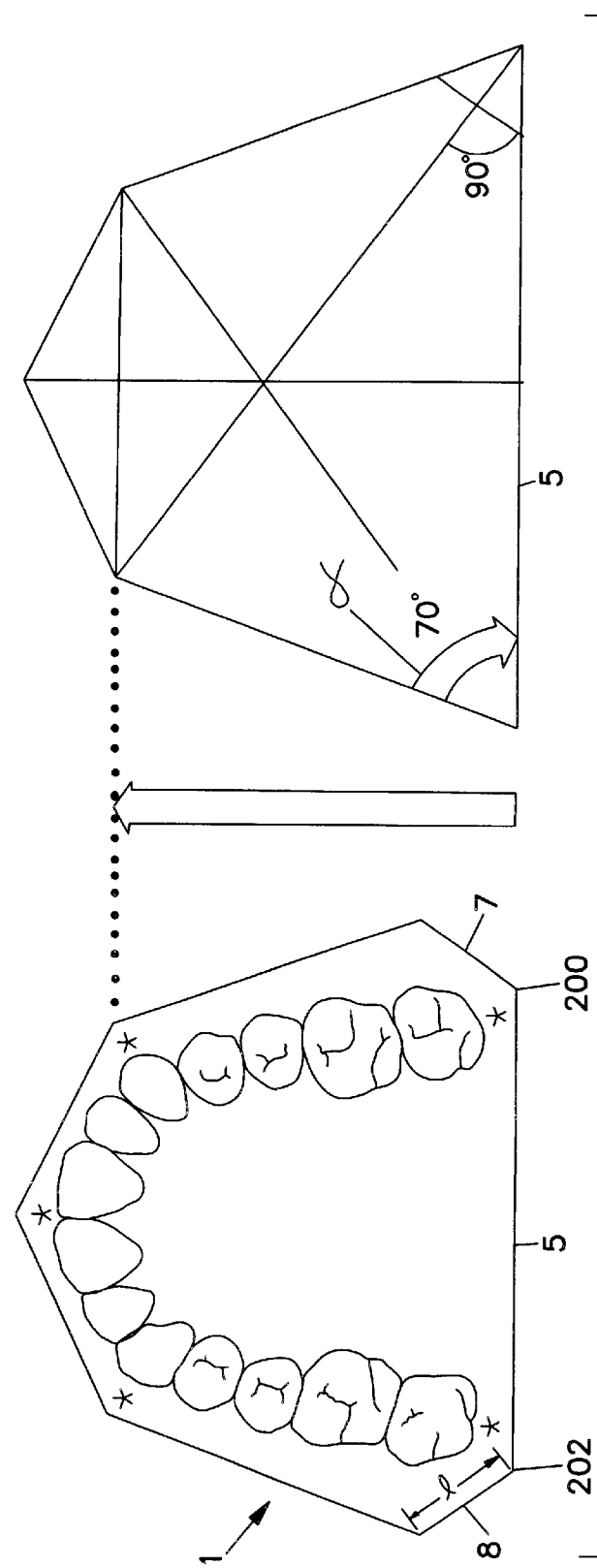
FIGS. 2A and 2B are top and schematic views of the maxilla and mandible study casts, respectively.
Figure 2B:
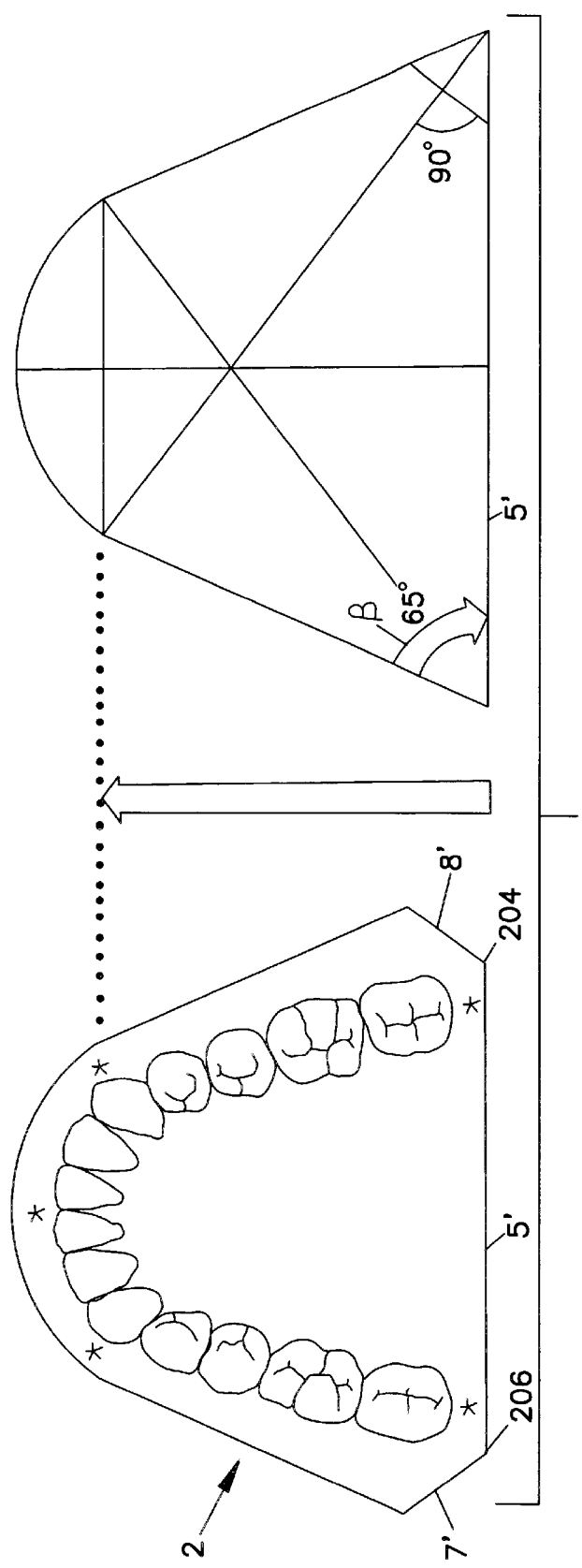
Figure 3:
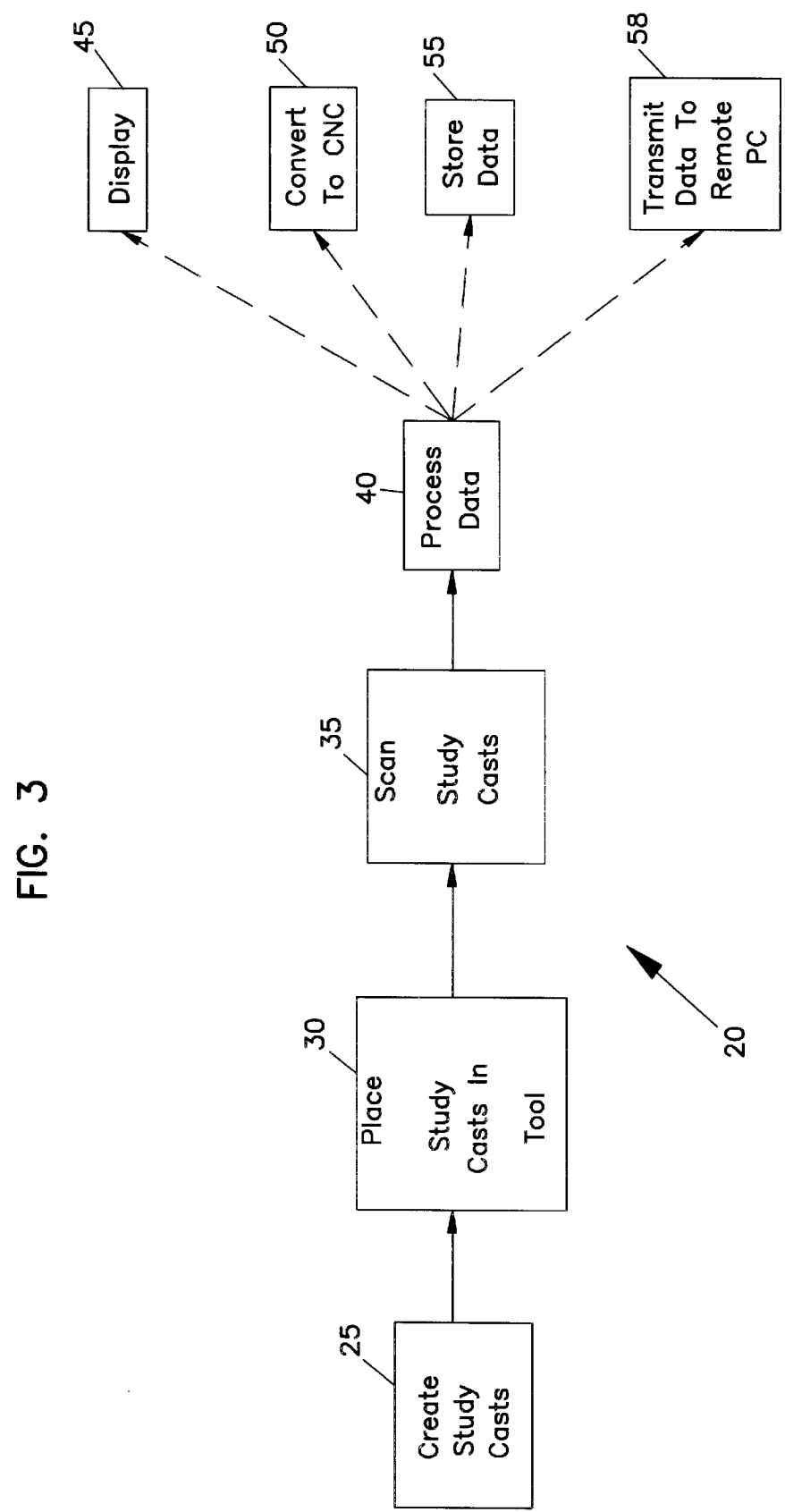
FIG. 3 illustrates a method of creating scanned images of dental study casts.

Referring first to FIG. 3, the overall method of creating images of scanned dental study casts is illustrated generally by the designation 20. First, at block 25, the maxilla and mandible plaster study casts to be scanned are created. The plaster study casts, such as those illustrated in FIGS. 1A, 1B, 2A and 2B are created according to ABO guidelines based upon negative impressions that are taken of a patient's teeth and surrounding gum tissue. The study casts useable with the present invention can also be roughly formed from plastic or other material, not in accordance with ABO guidelines.

Figure 4:
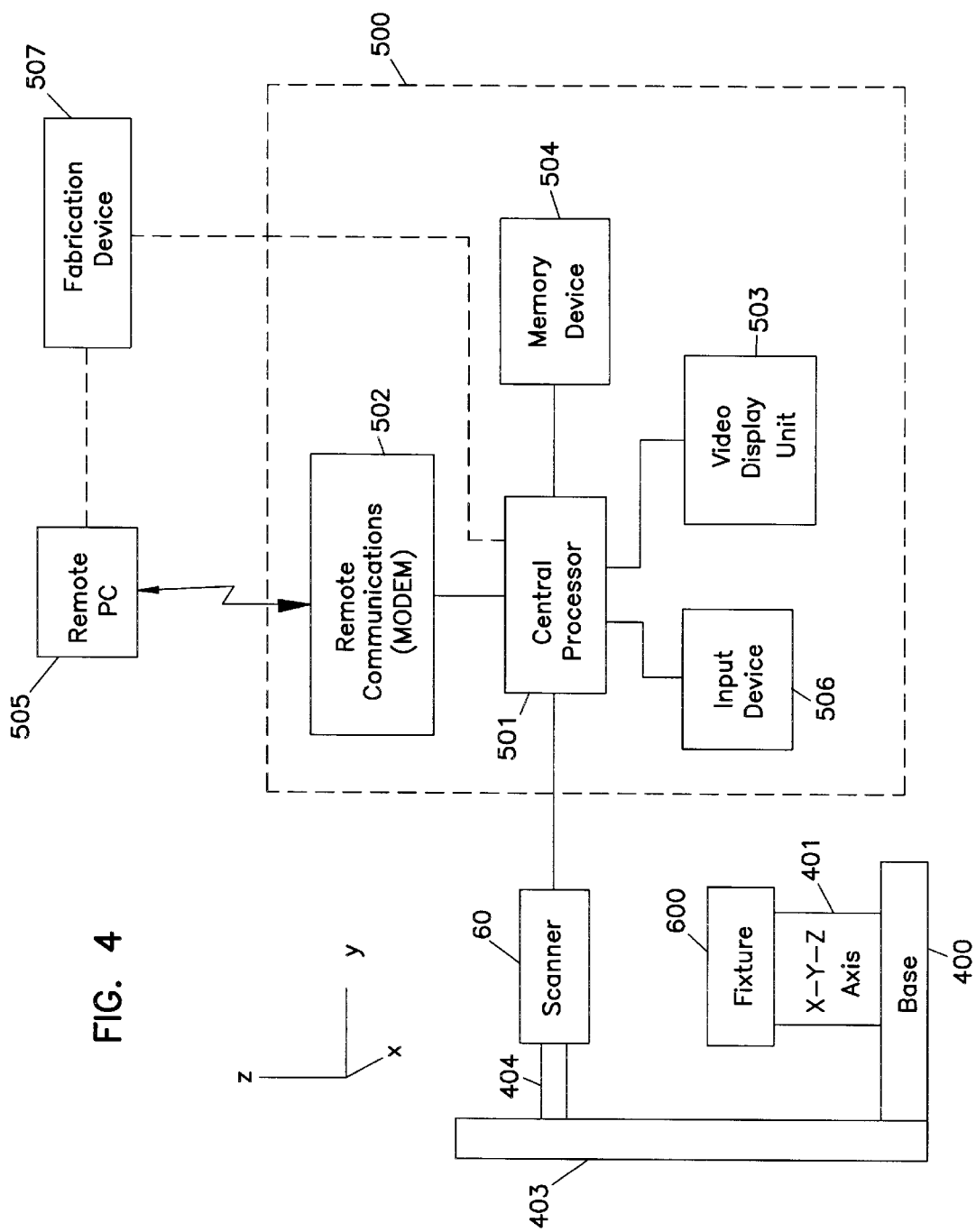
FIG. 4 diagrammatically illustrates a scanner used to perform scanning of the dental study casts, and the functional blocks associated with a processor, memory, and remote computer associated with processing the data from the scanner.

Next, at block 30, the study casts are placed in a tool or fixture 600 (described below and best seen in FIG. 4) of a scanning system that includes a scanner 60. The fixture 600 is used to securely hold the study casts during scanning. As schematically illustrated in FIG. 4, the fixture 600 is mounted on an x-y-z device 401 that moves the fixture 600 and the study casts mounted thereon along an x-axis (into and out of FIG. 4), a y-axis (left and right in FIG. 4), and a z-axis (up and down in FIG. 4) during scanning. The x-y-z device 401 is mounted on a base 400, and a column 403 attached to the base 400 supports the scanner 60 on the end of a mounting member 404.

Next at block 35, scanning of the study casts occurs. The scanner 60 is preferably a laser scanner that is capable of movements along the x-y-z axes to permit scanning of the complex geometries of dental study casts.

With reference to FIGS. 3 and 4, at block 40, the image data is processed by processor 501 of a computer 500 to create scanned images of the dental study casts. The processing at block 40 may include converting the scan data into images for display on a video display unit 503 (at optional block 45); converting the scan data into CNC or other format of output for use by a fabrication device 507 (also known as a prototyping apparatus)(at optional block 50); storing the scan data in a memory location or device 504 (at optional block 55); and/or transmitting the scan data to a remote processor 505 via modem block 502 (at optional block 58). A user input device 506 permits input commands to control operation of the scanner, as well as input information concerning the study casts to be scanned.

Further details on the scanning process and processing the image data can be found in U.S. Pat. Nos. 6,217,334, 6,206,693, and 6,200,135, which are incorporated herein by reference.

The scanner used in the present invention is preferably a laser scanner. However, other scanning concepts can also be used to practice the methods described herein, such as digitizing scanning.

The scanned images of the maxilla and mandible study casts are described as being displayed on display device 503, such as on a monitor of a personal computer. However, the scanned images must first be registered with each other so that the displayed image accurately portrays the existing static bite relationship of the patient's maxilla and mandible teeth. Therefore, suitable methodology is required to achieve registration of the scanned images.

2. Bite Registration

As noted above, after scanning of the dental study casts is complete, achieving an accurate bite registration of the scanned images of the maxilla (i.e. upper) and mandible (i.e. lower) study casts that are displayed on the display unit 503 is necessary. The following describes different methods according to the present invention by which bite registration can be achieved.

Method #1

Figure 5:
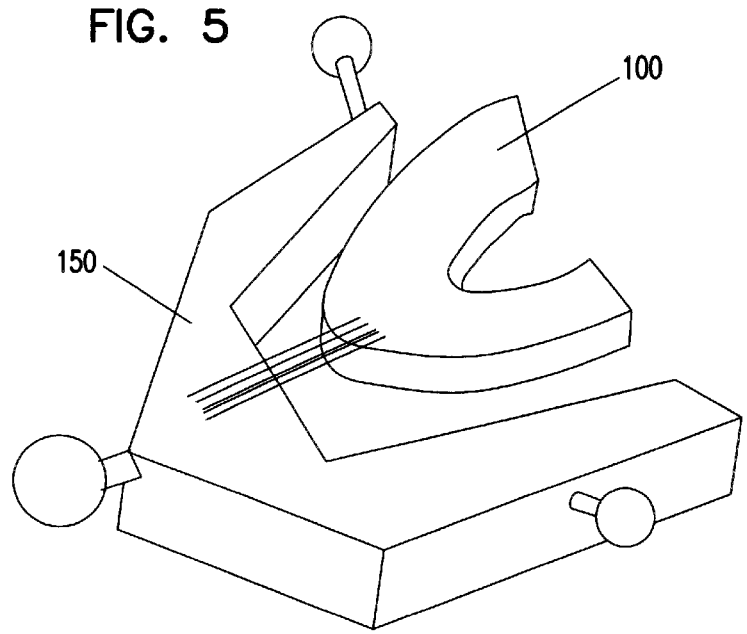
FIG. 5 illustrates a clutch tray and tooling used in implementing one method of the present invention.

This method utilizes a clutch tray 100, such as the clutch tray disclosed in U.S. Pat. No. 6,217,334, which is incorporated herein by reference. The clutch tray 100 simultaneously records a negative impression of the patients upper and lower teeth. Moreover, this method utilizes tooling 150 for securely holding the tray for subsequent scanning, such as tooling disclosed in U.S. Pat. No. 6,200,135, which application is incorporated herein by reference. FIG. 5 schematically illustrates the tooling 150 and the clutch tray 100. Tooling balls 152 provide fixed reference points for matching a scan of the upper impression of the tray 100 with a scan of the lower impression of the tray 100.

Figure 6:
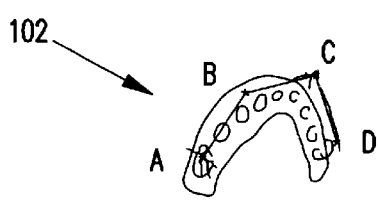
FIG. 6 is a schematic illustration of a scanned image of the upper clutch tray impression.
Figure 7:
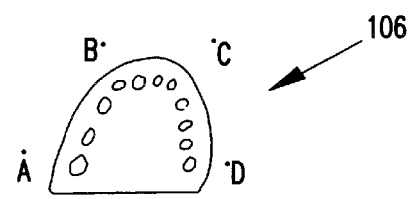
FIG. 7 is a schematic illustration of a scanned image of the upper study cast.
Figure 8:
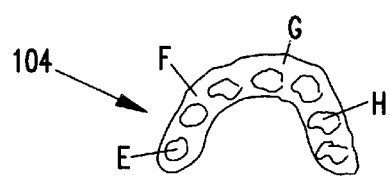
FIG. 8 is a schematic illustration of a scanned image of the lower clutch tray impression.
Figure 9:
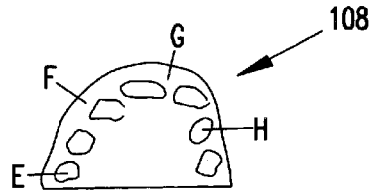
FIG. 9 is a schematic illustration of the scanned image of the lower study cast.

In practicing the first method, after a patient bites into the impression material on the clutch tray 100, thereby recording an impression of the patient's bite registration, the tray 100 is mounted on the tooling 150. The upper and lower impressions on the tray are then scanned, and visual images of the upper and lower impressions are created and displayed on the computer. FIGS. 6 and 8 schematically illustrate the scanned images 102, 104 of the upper and lower impressions, respectively. In addition, the upper and lower study casts are scanned. FIGS. 7 and 9 schematically illustrate the scanned images 106, 108 of the upper and lower study casts. Four prominent points, such as points A–D and E–H, are selected on each of the scanned images 102, 104 of the upper and lower impressions displayed on the computer, as shown in FIGS. 6 and 8 for the upper impression image and the lower impression image. In addition, the same four corresponding points on the upper and lower study cast images 106, 108 are also selected. A number of points smaller than four can be used, but the accuracy of the resulting registration is reduced. Further, a number of points larger than four can also be used, with a resultant larger number of data points to be selected and aligned.

By aligning the four points on the upper impression image 102 with the four corresponding points on the upper study cast image 106, and aligning the four points on the lower impression image 104 with the corresponding four points on the lower cast image 108, an accurate bite registration of the upper and lower scanned images is achieved. The selection and alignment of the points is done manually on the computer by an operator through the input device. The images are displayed on the display unit with the images of the upper and lower impressions disposed between the images of the upper and lower casts. The operator manipulates the images on the computer to achieve alignment of the points. Typically, the images would be displayed and viewed on the display unit in superimposed top or bottom plan views (e.g. see FIG. 13 discussed supra) in order to align the points. Once the points are aligned, the images of the upper and lower impressions are removed, leaving the upper and lower cast images in registration.

Figure 10:
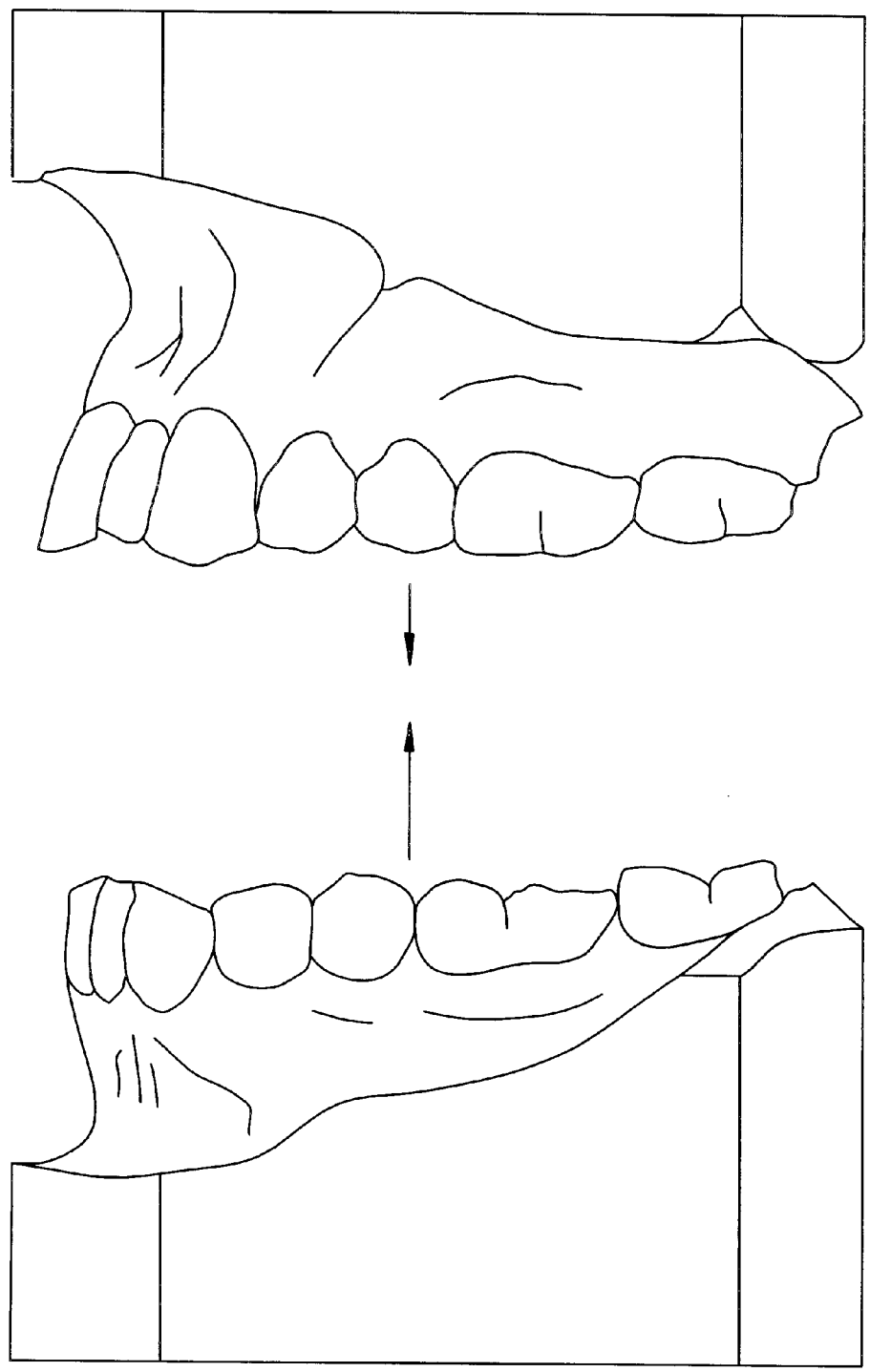
FIG. 10 is a side plan view of the upper and lower scanned images that are to be brought together to a position representing the patient's bite registration.

Once the cast images are registered, the registered images are moved toward each as illustrated in the side view of FIG. 10 until a position is reached representative of the patient's bite registration. The criteria that is used to determine the position that represents the patient's bite registration (i.e. the extent to which the images are brought together) can vary depending upon the accuracy that is required in the display. In one implementation, the upper and lower scanned images can be brought together and then stopped once the first point of contact between the scanned images is reached. The first point of contact of the scanned images would replicate the first point of contact between the patient's teeth during a bite. Preferably, the scanned images are brought together until a predetermined number of contact points are achieved between the two images. The number of contact points is predetermined for each different application and thus the number of contact points can vary. For registering other objects, such as housing shells as discussed below, one could utilize a percentage of contact area to determine how far the objects are brought together.

This method relies upon operator manipulation of the displayed images to achieve registration once the study casts and clutch tray scans are complete. Precise positioning of the study casts on their support structure is not required. Instead, because registration is achieved manually once the scan images are created, positioning of the study casts on the support structure can be random.

This method is relatively time and labor intensive in that it requires scanning of the clutch tray, in addition to scanning of the study casts, as well as requiring manual manipulation of the displayed images to achieve registration.

Method #2

Figure 12:
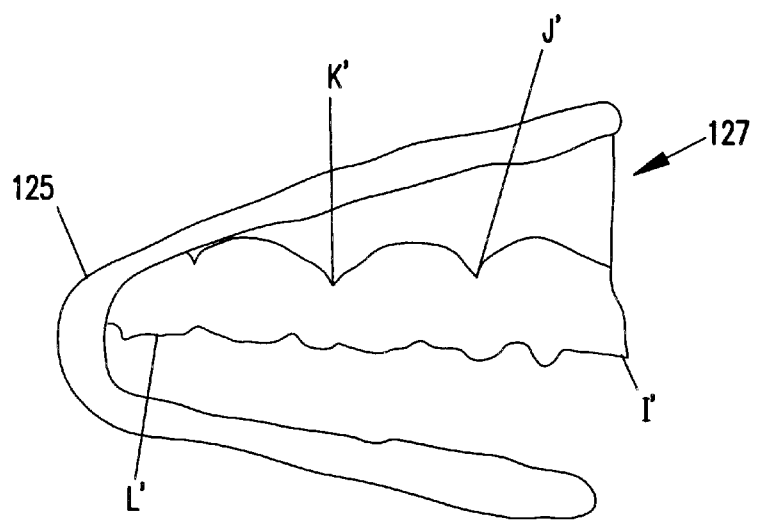
FIG. 12 schematically illustrates the scanned image of the upper portion of a buccal impression recorded by a buccal impression apparatus.

This method utilizes impressions that are recorded by a buccal impression registration apparatus to achieve registration of the scanned dental study cast images. A suitable buccal impression registration apparatus is disclosed in U.S. Pat. No. 6,206,693, which application is incorporated by reference. FIG. 12 schematically illustrates an exemplary buccal apparatus 125. As described in U.S. Pat. No. 6,206,693, a buccal impression registration apparatus is advantageous in that it permits the bite registration of the upper and lower dentitions to be recorded when the upper and lower dentitions are in contact with each other. Therefore since no material is disposed between the upper and lower dentitions, a more accurate recording of the bite registration can be obtained. Further, by forming an impression of only a portion of the upper and lower dentitions, the surface area that needs to be scanned is reduced while still obtaining an accurate recording of the bite registration. One buccal apparatus is used to record an impression of a portion of the upper and lower dentitions on one side of the mouth, while a second buccal apparatus is used to record the impression on the other side of the mouth.

Figure 11:
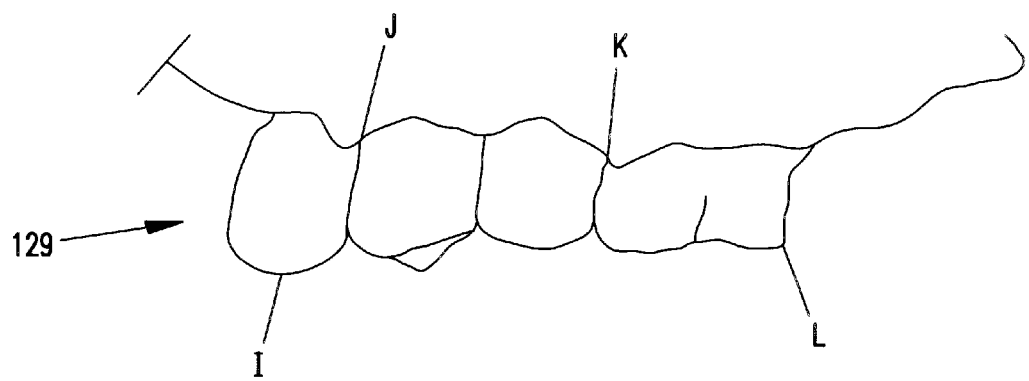
FIG. 11 schematically illustrates a portion of the scanned image of the upper study cast.

In practicing the second method, once the impressions are recorded by the first and second buccal apparatus, each buccal apparatus is mounted on tooling for scanning. The impressions are then scanned, and visual images of the scanned impressions are created and displayed on the computer. FIG. 12 schematically illustrates the scanned image 127 of just the upper portion of the recorded buccal impression. In addition, the upper and lower study casts are scanned. FIG. 11 schematically illustrates a portion of the scanned image 129 of the upper study cast that corresponds to the portion recorded by the buccal apparatus 125. Four prominent points, such as points I–L are selected on the scanned image 129 of the upper study cast displayed on the computer, as shown in FIG. 11. In addition, the same four corresponding points I'–L' on the scanned image of the buccal impression portion are also selected. This process is repeated for the lower portion of the recorded buccal impression and the corresponding portion of the scanned image for the lower study cast. In addition, this process is repeated for the other side of the patients mouth as well.

By aligning the four points I–L on the image 129 with the four corresponding points I'–L' on the image 127, aligning the four points on the lower portion of the recorded buccal impression and the four points corresponding portion of the scanned image for the lower study cast, and aligning the points on the other side of the mouth, an accurate bite registration of the upper and lower scanned images is achieved. Thus, a total of sixteen points are selected and aligned for each side of the mouth. The selection and alignment of the points is done manually on the computer by an operator through the input device. The images are displayed on the display unit with the images of the buccal impressions disposed adjacent the images of the upper and lower casts. The operator shifts the upper and lower cast images on the computer to achieve alignment of the points. Once the points are aligned, the images of the buccal impressions are removed, leaving the upper and lower cast images in registration. The images are then brought together in the manner discussed for method #1 to a position representative of the patient's bite registration.

As for method #1, the second method relies upon operator manipulation of the displayed images to achieve registration once the study cast and buccal impression scans are complete. Precise positioning of the study casts on their support structure is not required. Instead, because registration is achieved manually once the scan images are created, positioning of the study casts on the support structure can be random.

This method is also relatively time and labor intensive in that it requires scanning of each buccal apparatus, in addition to scanning of the study casts, as well as requiring manual manipulation of the displayed images to achieve registration. The extent of the impressions recorded by the buccal apparatus are limited in extent thereby reducing the area to be scanned. In addition, more points need to be selected and aligned in the second method as compared to the first method, thereby resulting in increased operator input and registration time compared to the first method. However, the use of the buccal apparatus permits an increase in the accuracy of the resulting registration.

The second method has been described with respect to the alignment of four points. At least three points are required to be used, but this reduces the accuracy of the resulting registration. Further, a number of points larger than four can also be used. However, this results in a larger number of data points to be selected and aligned.

Method #3

This method utilizes the precise geometry of the machined plaster study casts 1, 2 of FIGS. 1A, 1B, 2A, and 2B to achieve registration of the scanned images of the study casts. Because the study casts 1, 2 are machined to precise specifications governed by ABO guidelines, certain points on the study casts provide convenient reference markers which can be used to achieve registration. In particular, as shown in FIGS. 2A and 2B, the edges 200, 202 between the rear surface 5 and the angled surfaces 7, 8 on the study cast 1, and the edges 204, 206 between the rear surface 5 and the angled surfaces 7', 8' on the study cast 2 provide consistent reference points that can be used to achieve effective registration of the scanned images.

With reference to FIG. 13, in implementing this method, the plaster study casts 1, 2 are fixed onto a cassette 210 which in turn is mounted onto the fixture 600 for subsequent scanning of the study casts. Mounting the study casts onto the cassette 210 permits both study casts to be scanned in a single scanning routine, thereby saving time by eliminating the need to mount one study cast for scanning and then removing that study cast after scanning and mounting the next study cast for scanning. Further, the cassette 210 is useful in implementing an automated scanning system.

The positioning of the study casts 1, 2 on the cassette 210 is not critical, as long as the study casts are able to be scanned by the scanner 60. However, it is important that the study casts 1, 2 be rigidly fixed onto the cassette 210 in such a manner that the study casts do not move or shift during the scanning process. If the study casts 1, 2 do move relative to the cassette 210 during scanning, the subsequently created scanned image will be distorted as a result of the movement. One way of fixing the study casts onto the cassette 210 is by the use of hot melt glue applied to the bottom surfaces 6, 6' of the study casts. The use of hot melt glue is a relatively inexpensive, effective means for fixing the study casts to the cassette 210. Further, hot melt glue permits detachment of the study casts from the cassette once scanning is complete, thereby allowing the cassette 210 to be reused for another set of study casts. Other means for fixing the study casts onto the cassette can also be utilized, such as by the use of releasable clamping mechanisms and the like. It is further contemplated that this method could be implemented by mounting and scanning the study casts separately. However, as discussed above, this would result in increased labor and time.

Once the study casts 1, 2 are mounted on the cassette 210 and the cassette is mounted on the fixture 600 of the scanner, the study casts are scanned to create scanned images 212, 214 of the upper and lower study casts, as schematically illustrated in FIG. 14. Registration of the images 212, 214 is achieved by manipulating the scanned images on the display unit 503 so that the edge 200 on the image 212 is vertically aligned with the edge 206 on the image 214 along the vertical line A (extending into and out of the page) in FIG. 14, and the edge 202 on the image 212 is vertically aligned with the edge 204 on the image 214 along the line B (extending into and out of the page) in FIG. 14. Once the edge are aligned, the images 212, 214 can be brought together on the display unit 503 as described above for method #1.

This method is simpler to implement than methods #1 and #2 as the points (e.g. edges 200–206) that are used to achieve registration are essentially preselected based upon the standard design of the plaster study casts. Further, because the bases of the study casts are based on a standard design, the computer can be instructed to look for the edges 200, 206 and 202, 204 and align the edges automatically without operator manipulation of the images. Therefore, this method could be used to automate the scanning and registration process. However, as discussed above, plaster study casts are expensive and labor intensive due to the precise machining requirements.

Method #4

This method can be used with the machined plaster study casts 1, 2. More preferably, this method is used with study casts 250, 252 that have roughly formed (i.e. not machined to precise geometric specifications) bases. In this method, the study casts 250, 252 are initially mounted on a cassette 254 in known locations relative to each other, prior to scanning. Because the positioning of each study cast relative to the other is known, once scanning is complete, the scanned images can be brought into registration using predetermined reference points.

Figure 15:
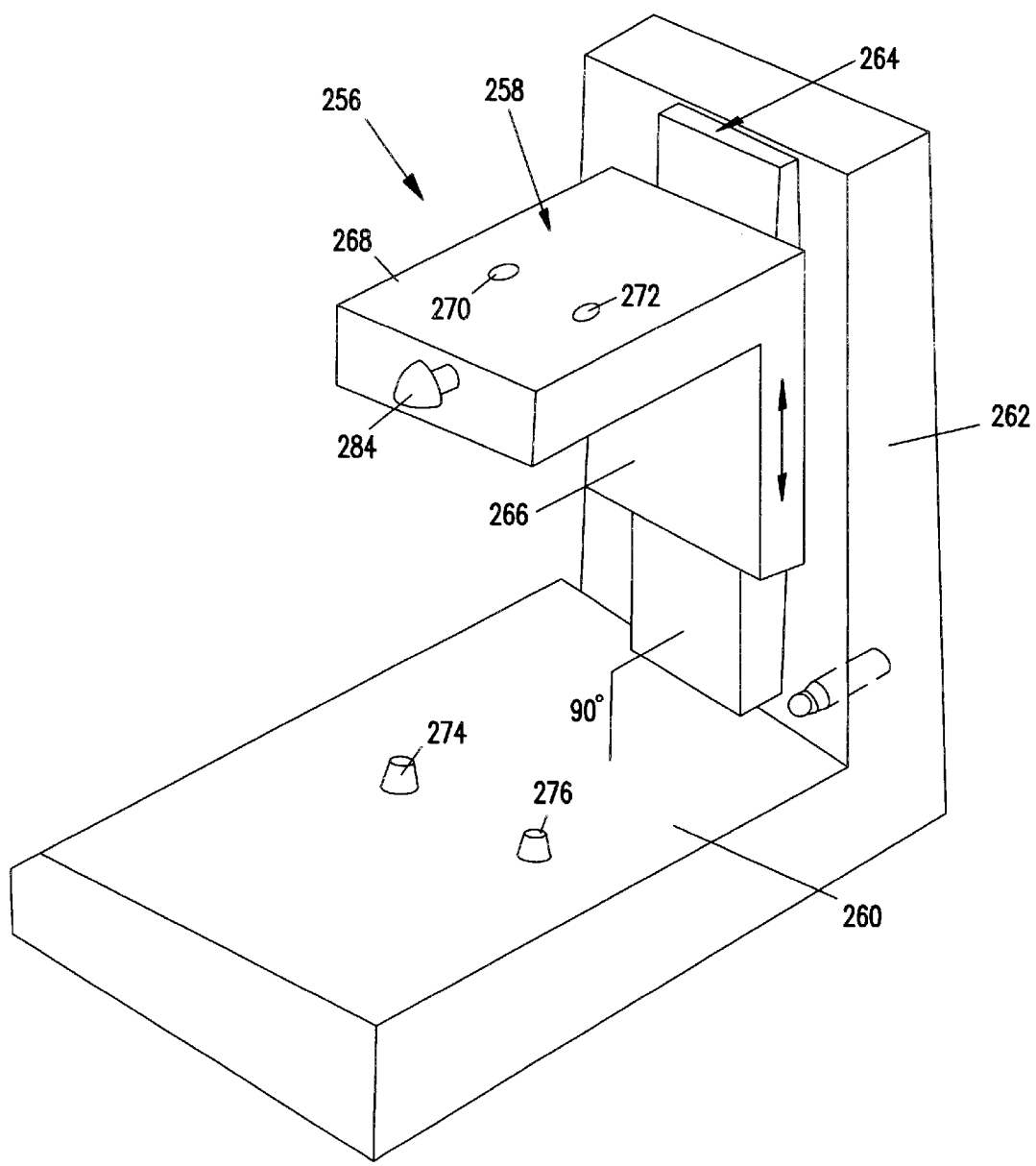
FIG. 15 illustrates a tool used to implement yet another method according to the present invention.

FIGS. 15–18 illustrate tooling and other apparatus used to implement this method. FIG. 15 illustrates a tool 256 that is provided with a precision vertical slide 258 that is mounted so as to move vertically up and down relative to the tool 256. The tool 256 includes a base 260 and a vertical support 262 provided with a guide rail 264. The slide 258 includes a base 266 that is slidable on the rail 264 and an arm 268 that overhangs the base 260. The arm 268 includes a pair of locating holes 270, 272 on the bottom surface of the arm 268 facing the base 260. The base 260 includes a pair of locating pins 274, 276.

Figure 16:
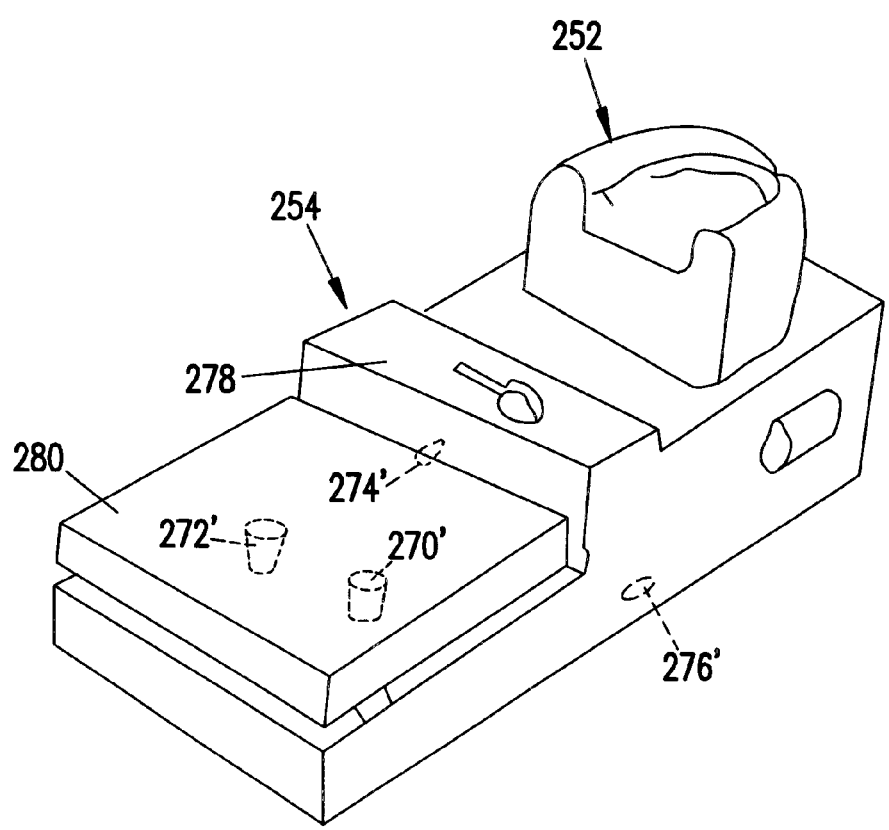
FIG. 16 illustrates a cassette used with the tool of FIG. 15.

FIG. 16 illustrates the cassette 254 upon which the study casts 250, 252 are to be mounted. The study cast 252 is schematically illustrated in position on the cassette 254. The cassette 254 includes a ridge 278 that separates the cassette into two halves, the first half receiving the study cast 252 and the second half receiving the study cast 250. A removable plate 280, upon which the study cast 250 is to be mounted, is provided on the second half of the cassette 254. A pair of locating holes 274', 276' are formed in the bottom of the cassette 254 which interact with the locating pins 274, 276, respectively, so as to permit mounting of the cassette onto the base 260 of the tool 256. In addition, the removable plate 280 includes a pair of locating pins 270', 272' formed on the bottom thereof that are designed to fit within the locating holes 270, 272, respectively, on the arm 268 of the slide 258. The second half of the cassette 254 includes holes (not visible) that receive the locating pins 270', 272' when the plate 280 is disposed on the cassette.

Figure 18:
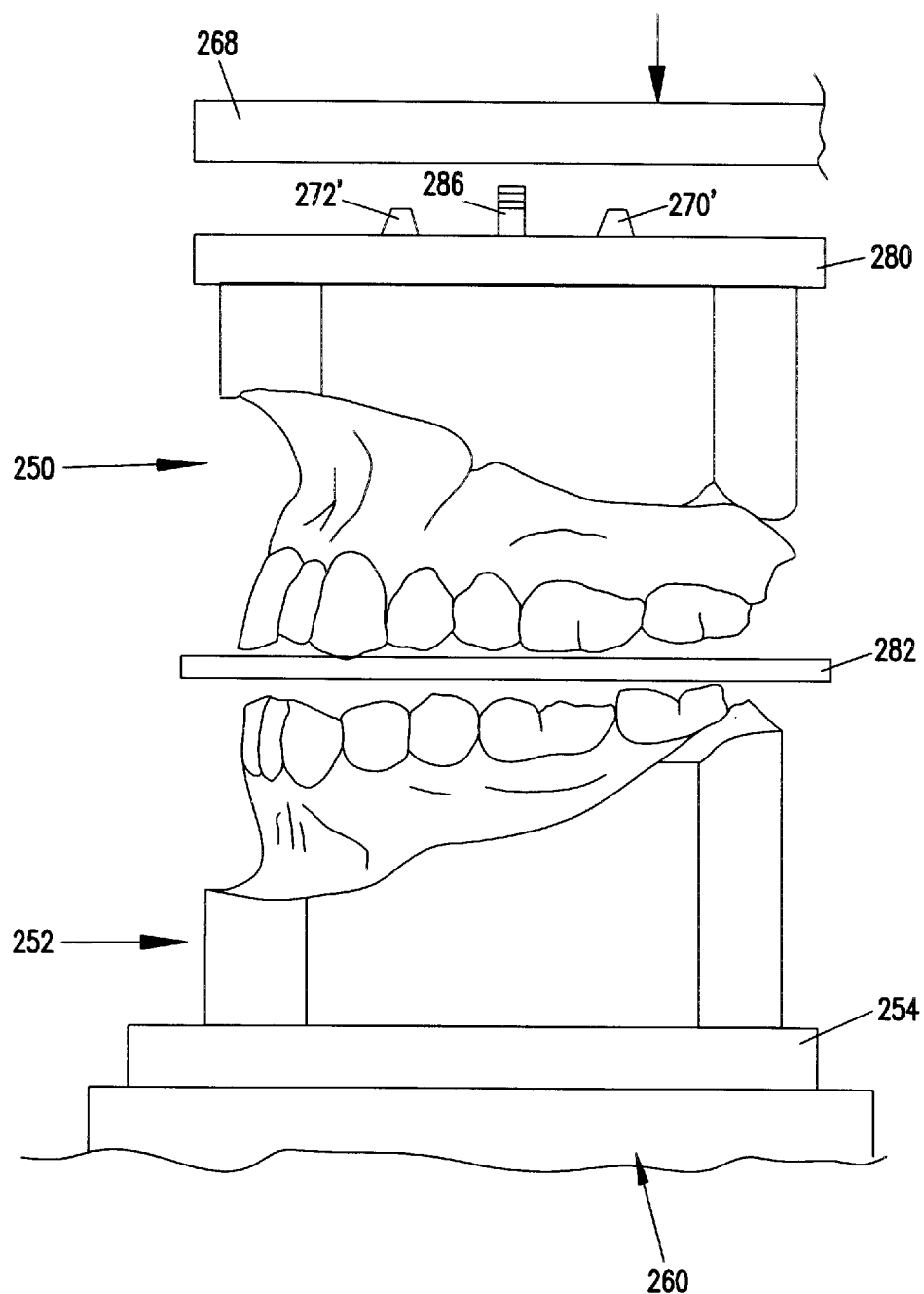
FIG. 18 schematically illustrates the use of the tool and cassette in FIGS. 15 and 16.

With reference to FIG. 18, in implementing method #4, the study cast 252 is first fixed onto the first half of the cassette 254 such as by using the hot melt glue mentioned with respect to method #3. The cassette 254 is then mounted onto the base 260 of the tool 256 via the locating pins 274, 276 and locating holes 274', 276', with the study cast 252 disposed underneath the arm 268 of the slide 258.

A wax wafer 282, or other similar impression material, which has been previously bit into by the patient corresponding to the study casts 250, 252 to record the patient's bite registration, is then placed onto the study cast 252. The wafer 282 is placed onto the study cast so that the impression that corresponds to study cast 252 fits onto the teeth of the cast 252. The study cast 250 is then placed on top of the wafer 282 with the teeth fitting into their corresponding impression in the wafer. It should be realized that the wafer 282 permits the study casts 250, 252 to be registered with each other while on the tool 256. Once the study casts are registered, the plate 280 is fixed onto the bottom surface of the study cast 250 such as by using hot melt glue or other fixing means.

The slide 258 is then slid downward, either manually using a knob 284 fixed to the arm 268 or through suitable mechanical means (not illustrated), toward the plate 280. The arm 268 then captures the plate 280, with the locating pins 270', 272' fitting into the locating holes 270, 272. A fastener 286 connected to the plate 280 extends upwardly through a hole provided in the arm 268 to permit the plate 280, and the study cast 250 now fixed thereto, to be fixed to the arm 268 so when the slide 256 is again raised, the study cast 250 and plate 280 are raised with the slide 256. Raising the slide 256 separates the study casts 250, 252 while precisely maintaining the relative positioning of the study casts so that the registration is maintained.

After the slide 258 is raised, the plate 280, with the study cast 250 fixed thereto, is removed from the arm 268, flipped over so that the study cast 250 faces upward, and mounted onto the second half of the cassette 254 so that both study casts are now fixed on the cassette. The study casts can then be scanned to create the scanned images as discussed above for method #3. It should be realized that the study casts are mounted on the cassette 254 in positions that maintain the bite registration of the patient. However, what is also needed are reference points so that the images can be aligned.

Figure 17:
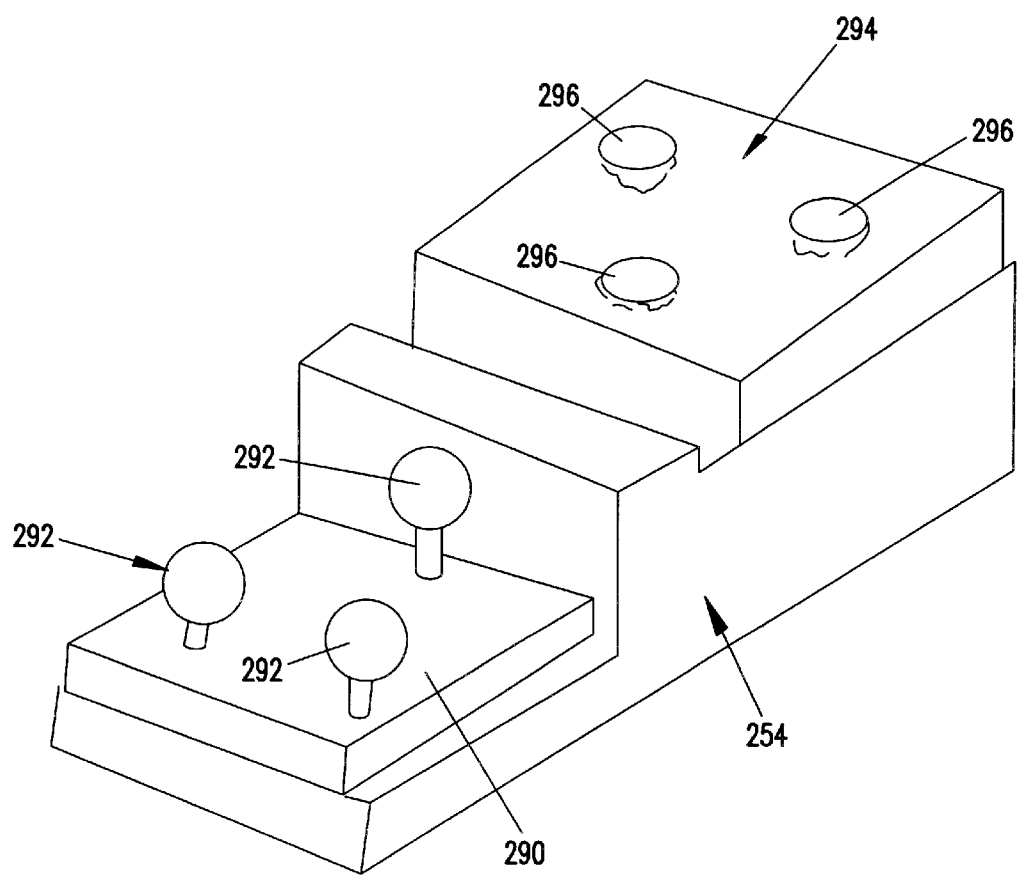
FIG. 17 illustrates a calibration procedure for determining reference points.

Reference points used in this method are achieved in accordance with a calibration process illustrated in FIG. 17. The calibration process is performed prior to mounting the study casts on the cassette. To perform calibration, the cassette 254 is provided with a removable plate 290, in place of the plate 280. The plate 290 includes a plurality of tooling balls 292 thereon. In the preferred embodiment, three tooling balls 292 are used, however a larger number of tooling balls could also be used. A layer of clay 294 or other impression material is placed on the other half of the cassette 254. The cassette 254 is mounted on the tool 256 as discussed above, with the clay 294 located underneath the arm 268, and the plate 290 is mounted on the arm 268 with the tooling balls 292 facing downward toward the clay 294. The slide 258 is then moved downward until the balls 292 move into the clay 294 in order to form tooling ball impressions 296. The slide 258 is then moved upwardly and the plate 290 removed therefrom and remounted onto the cassette 254.

The cassette 254 is then mounted on the fixture of the scanner and the scanner scans the tooling balls 292 and the impressions 296. By scanning the tooling balls 292 and impressions 296, the system can find the centers of the balls 292 and impressions 296, with the centers providing fixed reference points for use in aligning the subsequently scanned study casts. These fixed reference points are retained within the memory device 504, so that the system knows ahead of time the reference points to be used. Due to the construction of the tool 256 and the cassette 254, the relative positions of the centers of the tooling balls 282 and the centers of the impressions 296 correspond to identical positions on the study casts 250, 252. Therefore, once the images of the study casts are generated, the three fixed points can be aligned to register the scanned impressions. After the points are aligned, the scanned images can be brought together to a position representative of the patient's actual bite registration. The reference points are fixed in system memory, so that once the study casts are properly positioned on the cassette 254, the scanning and registration can be completed automatically, without requiring further operator input. It is further contemplated that the use of the tool and the related process of positioning the study casts on the cassette 254 can be automated as well.

Periodically, the calibration process should be repeated so as to obtain updated reference points. This is necessary due to loosening of tolerances and general degradation of equipment.

A benefit to this method is that is can be used with roughly formed study casts, thereby eliminating the expense and labor associated with machining plaster study casts. This method can also be more readily implemented with automated scanning concepts.

The previous four methods have been described in relation to scanning and registering dental study casts. However, as discussed above, the concepts described herein can also be used to scan and register a variety of parts that are to be mated together, such as molded housing shells for cellular phones, electronic organizers, pacemakers, and a host of other parts having complex geometries. When applied to mated parts, the accuracy of the parts, and the molds used to create the parts, can be verified to determine whether a suitable fit between the parts will be achieved. This verification can be performed at the manufacturing level by the supplier of the molded parts as the molded parts are molded, or at an assembly level by the user of the molded parts to ensure quality of received parts. Molded parts can include plastic molded parts, metal parts formed by metal molding techniques, and mating parts formed from other materials and other molding techniques suitable for those other materials.

Figure 19:
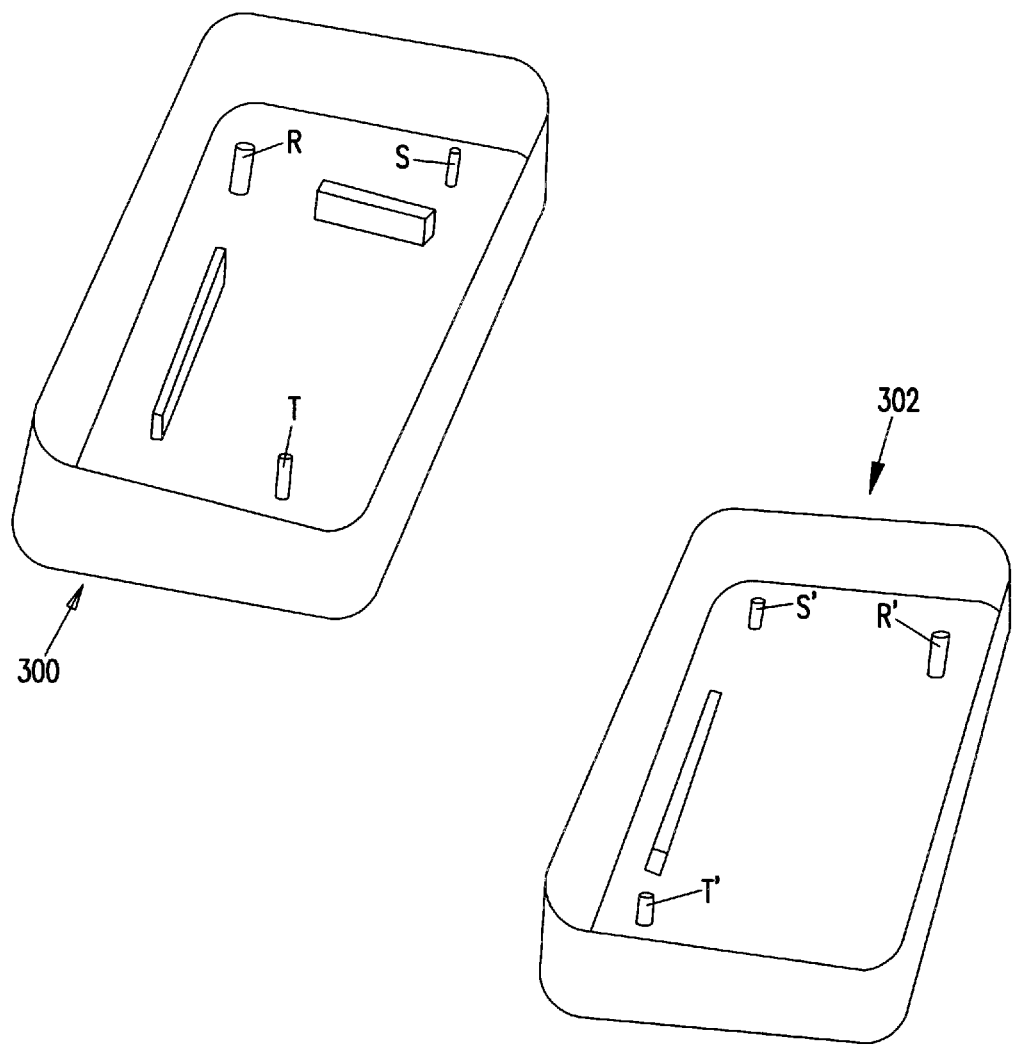
FIG. 19 schematically illustrates a pair of housing shells to be scanned to verify their mating relationship.

FIG. 19 illustrates a pair of housing shells 300, 302 that are to be mated together to form a housing for a device such as a cellular phone, electronic organizer or a pacemaker. The inside of each housing shell 300, 302 is schematically illustrated to show an example of the possible complex geometry inside each shell. In use, the shell 300 is flipped over and mated with the shell 302 to enclose the electronics and other components of the device formed by the mated shells 300, 302.

The concepts of the four methods described above with respect to dental study casts can be utilized to scan the shells 300, 302 and display their mating relationship (i.e. "verify" the parts) to determine whether the shells fit together adequately. A plurality of reference points would have to be used to achieve alignment of the shell images once they are scanned. For instance, three points R, S, T on the shell 300, and three points R', S', T' on the shell 302, corresponding to, for example, mounting posts on the shells 300, 302, could be used to align the images once the shells are scanned. Method #4 described above could also be used to scan and register the shells 300, 302.

While a particular embodiment of the invention has been described, it will be understood that by those skilled in the art that the invention is not limited by the application, embodiment or the particular devices disclosed and described herein. It will be appreciated that other devices that embody the principles of this invention and other applications therefore other than as described herein can be configured within the spirit and intent of this invention. The systems and apparatus described herein are provided as only examples that incorporates and practices the principles of this invention. Other modifications and alterations are well within the knowledge of those skilled in the art and are to be included within the broad scope of the appended claims.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A bite registration method for maxilla and mandible study casts, comprising:

positioning the maxilla and mandible study casts on a cassette;

scanning the maxilla and mandible study casts while they are on the cassette to create maxilla and mandible study cast images; and registering the maxilla and mandible study cast images.

2. The bite registration method according to claim 1, wherein registering the maxilla and mandible study cast images comprises aligning a plurality of reference points.

3. The bite registration method according to claim 2, wherein the reference points are associated with the maxilla and mandible study cast images.

4. The bite registration method according to claim 3, further including recording at least a partial impression of the bite registration of a patient's teeth corresponding to the study casts.

5. The bite registration method according to claim 4, wherein the at least partial impression comprises a buccal impression.

6. The bite registration method according to claim 4, wherein the at least partial impression is scanned to create an impression image.

7. The bite registration method according to claim 6, further including selecting reference points from the impression image.

8. The bite registration method according to claim 2, wherein the study casts are machined plaster study casts, and the reference points are selected from predetermined edges on the study cast images.

9. The bite registration method according to claim 2, wherein the reference points are determined prior to scanning the study casts.

10. The bite registration method according to claim 9, further including positioning the study casts on the cassette in known positions relative to each other.

11. The bite registration method according to claim 2, further comprising bringing the registered maxilla and mandible study cast images together to a position representative of the bite registration of the patient's bite registration.

12. The bite registration method according to claim 11, wherein the images are brought together up to at least the point of first contact between the maxilla and mandible study cast images.

13. The bite registration method according to claim 11, further including displaying the registered maxilla and mandible study cast images on a display device.

14. A bite registration method for maxilla and mandible study casts, comprising:

providing a cassette;

mounting the maxilla and mandible study casts on the cassette in a predetermined spatial relationship relative to each other;

scanning the maxilla and mandible study casts while they are on the cassette to create maxilla and mandible study cast images; and registering the maxilla and mandible study cast images.

15. The bite registration method of claim 14, comprising determining the bite registration of the maxilla and mandible study casts, and the predetermined spatial relationship comprises positions on the cassette that maintain the bite registration of the study casts.

16. The bite registration method of claim 15, comprising determining a plurality of reference points associated with the cassette prior to mounting the study casts on the cassette.

17. The bite registration method of claim 16, comprising storing the reference points in memory.

18. The bite registration method of claim 16, comprising updating the reference points on the cassette.

* * * * *